United States Patent [19]

Wardlaw et al.

[11] Patent Number: 5,171,528
[45] Date of Patent: Dec. 15, 1992

[54] DEVICE FOR DIFFERENTIATING THE SOURCE OF OCCULT GASTRO-INTESTINAL BLEEDING

[76] Inventors: Stephen C. Wardlaw, 128 Sunset Hill Dr., Branford, Conn. 06405; Robert A. Levine, 31 Pilgrim La., Guilford, both of Conn. 06437

[21] Appl. No.: 740,289

[22] Filed: Aug. 5, 1991

Related U.S. Application Data

[62] Division of Ser. No. 423,181, Oct. 18, 1989, Pat. No. 5,064,766.

[51] Int. Cl.⁵ ...................... G01N 21/78; G01N 33/72
[52] U.S. Cl. ........................ 422/56; 128/638; 128/759; 210/193.3; 422/58; 422/61; 422/70; 436/66; 436/162; 436/169; 436/170; 436/178; 435/805
[58] Field of Search ................ 436/66, 162, 169, 170, 436/175, 177, 178, 904; 422/56–58, 61, 70; 435/28, 805; 128/638, 749, 756, 759; 210/658, 198.3

[56] References Cited

U.S. PATENT DOCUMENTS

| | | | |
|---|---|---|---|
| 3,590,006 | 6/1971 | Page et al. | 436/162 |
| 3,714,035 | 1/1973 | Jones | 210/658 |
| 3,963,421 | 6/1976 | Jones | 436/162 |
| 4,438,205 | 3/1984 | Saint et al. | 436/162 X |
| 4,956,308 | 9/1990 | Wells | 436/66 |

Primary Examiner—Robert J. Hill, Jr.
Attorney, Agent, or Firm—Price, Heneveld, Cooper, DeWitt & Litton

[57] ABSTRACT

The specification discloses a fecal occult blood test device capable of determining whether the blood found during the test originated in the upper or lower gastro-intestinal track. A fecal sample is applied to a test medium charged to be differentially attractive to blood components originating in the upper and lower gastro-intestinal track respectively. A solvent is applied to the test specimen to cause differential migration of the blood components and an indicator is then applied to indicate the presence of the blood components, if any.

27 Claims, 4 Drawing Sheets

DEVICE FOR DIFFERENTIATING THE SOURCE OF OCCULT GASTRO-INTESTINAL BLEEDING

This is a division of application Ser. No. 07/423,181, filed Oct. 18, 1989, which issued Nov. 12, 1991, as U.S. Pat. No. 5,064,766.

BACKGROUND OF THE INVENTION

The present invention relates to testing for occult gastrointestinal bleeding. The common screening test for occult gastrointestinal bleeding is the test for fecal occult blood (FOB). This test involves placing a sample of stool onto a testing surface and adding one or more reagents which react with the blood in the sample to produce a recognizable color.

Two current varieties of such tests are the Hemoccult ® device and the HemaWipe ® device. The Hemoccult ® test device requires that one use a small paddle to fish a feces sample out of the toilet and apply the sample to a piece of test paper mounted on a card. U.S. Pat. No. 3,996,006 to Pagano is exemplary of a Hemoccult ® test device.

The HemaWipe ® device utilizes a test pad adhered to a pliant impermeable base sheet and covered with a pliant volume control sheet having openings therein in alignment with the test pad. The patient can wipe with the HemaWipe ® device, remove the volume control cover sheet, fold the pliant base sheet over on itself to seal the test pad and sample and submit it for testing. A number of prior patents relate to the HemaWipe ® device including U.S. Pat. No. 4,808,379, entitled "DEVICE FOR OBTAINING STOOL SAMPLES," issued Feb. 18, 1989, U.S. Pat. No. 4,804,518, entitled "DEVICE FOR OCCULT BLOOD TESTING," issued Feb. 14, 1989, U.S. Pat. No. 4,559,949, entitled "STOOL SAMPLING DEVICE," issued Dec. 24, 1985. U.S. Pat. No. 4,420,353, entitled "METHOD OF MAKING A STOOL SAMPLING DEVICE," filed Dec. 13, 1983, U.S. Pat. No. 4,367,750, entitled "DEVICE FOR OBTAINING STOOL SAMPLES," issued Jan. 11, 1983, U.S. Pat. No. 4,273,741, entitled "DEVICE FOR OBTAINING STOOL SAMPLES," issued Jun. 16, 1981, and U.S. Pat. No. 4,259,964, entitled "DEVICE FOR OBTAINING STOOL SAMPLES," issued Apr. 7, 1981.

Virtually all FOB tests used today have the problem of nonspecificity. Their chemical reactions detect the peroxidase property of hemoglobin by causing the catalysis of peroxide into oxygen and water, and the subsequent oxidation of a colorless dye into a colored form. Gum guaiac is the most commonly used color reagent, although a large number of other reagents have been used in the past.

The nonspecificity is due to two reasons. First, there are other peroxidase positive materials which the patient may eat, which, when excreted, will also cause a positive reaction. Secondly, there is a normal, small loss of blood into the GI tract which in some patients will escape into the stool in amounts large enough to cause a reaction. It is obvious that the more sensitive the reagent, the more sensitive the test, but the more likely that there will be a false-positive reaction.

The FOB tests are more frequently used to screen patients for a hidden colonic malignancy, so that the consequences of missing any bleeding can be severe. Conversely, if there are a large number of false-positive tests, the expense and possible complications of the additional follow-up tests involved are also considerable. There have been many attempts to make the FOB test more specific, and thus allow adequate sensitivity while preventing the undesired false-positive results.

Specific immunologic tests have been employed which are sensitive only to human blood. The problem with these have been that they are much more complicated and expensive than the usual screening test, and the blood may be altered by partial digestion so that it is not detected by immunologic means. A recent technique called Hemaquant involves the extraction of a stool sample to obtain porphyrins, the breakdown products of blood. The advantage of this technique is that it is quantitative and relatively specific, but it too is expensive and much more cumbersome than the usual screening tests.

An important consideration in any work-up for GI bleeding is the source. Where the FOB test is used to screen for colo-rectal cancer, the only blood of interest is from the lower GI tract. Blood from gastritis or dental bleeding would be considered a false-positive, even though blood was indeed present. It can therefore be seen that the concept of a false-positive test involves more than the incorrect detection of blood but also the circumstances under which it is detected. Ideally, an FOB test would not only reliably detect blood but also give some indication as to the origin of the blood.

It is therefore an object of this invention to provide a simple but accurate means of detecting a small amount of blood in a sample of stool. It is also a object of this invention to provide an indication of the origin of the blood.

SUMMARY OF THE INVENTION

The present invention is based on the fact that blood, as it passes through the GI tract, changes character in ways that allow the blood from various sites to be physically separated and detected. When blood (either from the patient or ingested) passes through the normal stomach, hydrochloric acid converts the relatively uncharged hemoglobin to hematin and related hemoglobin breakdown products (HBPs), which are highly charged.

In the present invention, a fecal sample is placed on a charged absorbant medium which will absorb hematin and/or other hemoglobin breakdown products and hemoglobin The medium is charged to be differentially attractive to hematin and hemoglobin breakdown products on the one hand and hemoglobin on the other. A solvent for hematin and/or other hemoglobin breakdown products and hemoglobin is then placed on the charged medium and allowed to migrate through the medium and through any material absorbed from the fecal sample to extract a detectable amount of hemoglobin and hematin and/or other hemoglobin breakdown products from the sample and to migrate through said medium. The hematin and any hemoglobin breakdown products tend to migrate more slowly than the hemoglobin due to the charge on the medium. Means for indicating hematin and/or other hemoglobin breakdown products and hemoglobin are then used to cause their visual detection.

The most obvious advantage of the foregoing invention is that it allows the doctor to determine whether fecal occult blood is originating in the upper GI or in the lower GI. If the blood is originating in the lower GI, further testing is called for. If it is originating in the upper GI, treatment for ulcers and/or dietary changes will be prescribed. A follow up fecal occult blood test performed several weeks later will indicate whether the treatment has been successful and if not, further tests can be conducted.

Also of interest, however, is that animal and vegetable peroxidases which constitute the usual dietary false-positives are also charged, like hematin and other hemoglobin breakdown products. Hence, these false-positive peroxidases also tend to "stick" to and are prevented from migrating through the medium.

Because of this, the test of the present invention can be made more sensitive by increasing the indicator dye concentration. In the prior art, the indicator dye is kept at a lesser concentration to avoid showing too many "false-positives" which result from dietary blood or dietary peroxidases. As a result, a substantial portion of fecal occult blood tests which are performed fail to show the presence of fecal occult blood originating in cancerous tumors in the lower intestine. By using the present invention, it is believed one can increase the concentration of indicator dye without encountering false-positives, and thereby greatly increase the sensitivity of the test to the presence of hemoglobin resulting from cancerous formations in the lower intestine.

These and other objects, advantages and features of the invention will be more fully understood and appreciated by reference to the written specification and appended drawings.

DESCRIPTION OF THE PREFERRED EMBODIMENT

Figures 1, 2, 3, 4, 5:
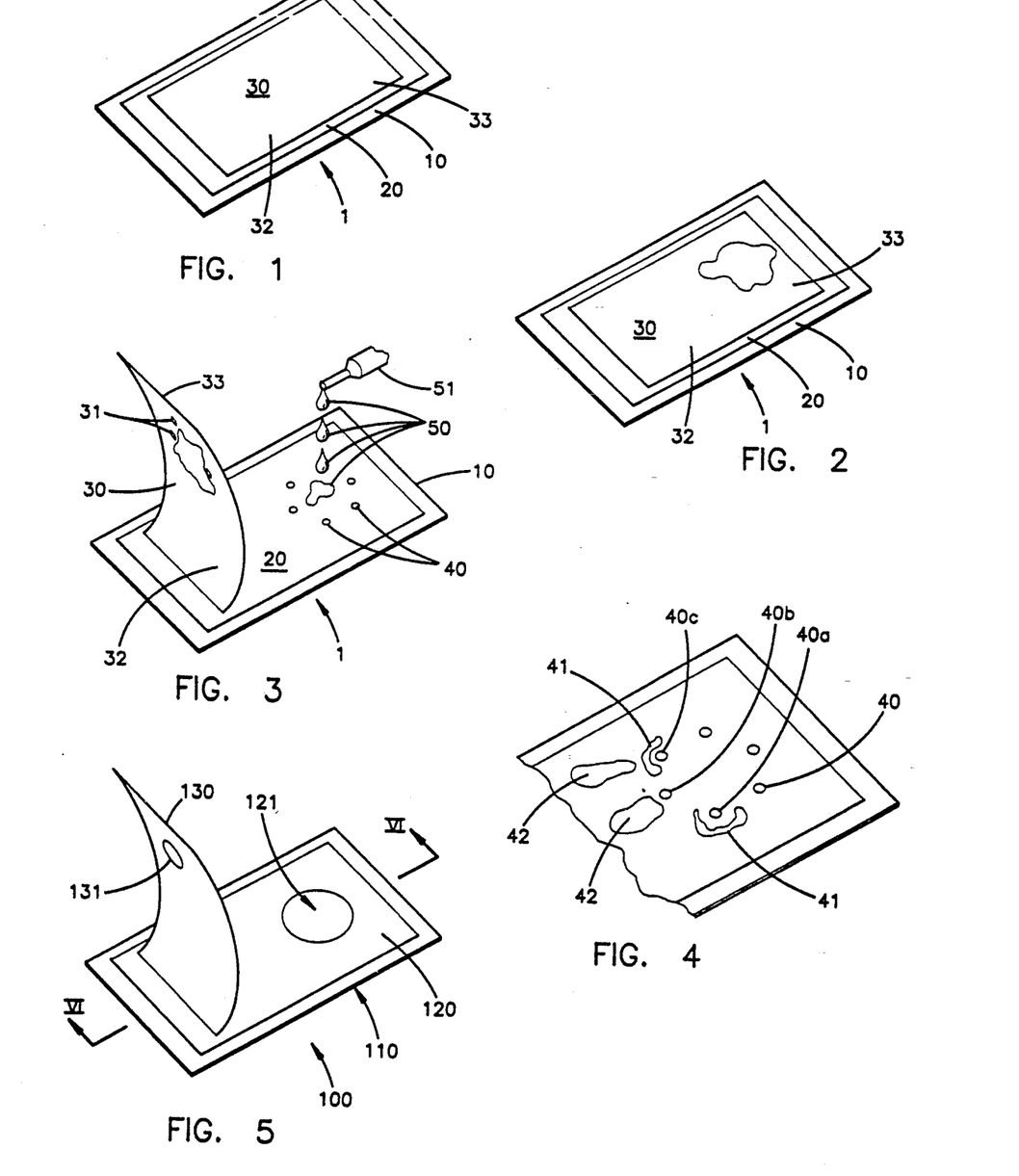
FIG. 1 is a perspective view of a fecal occult blood testing device made in accordance with the present invention.
FIG. 2 is a perspective view thereof after a fecal sample has been applied to the volume control top sheet thereof.
FIG. 3 is a perspective view of the device with the volume control sheet being removed and with solvent being applied to the absorbant medium.
FIG. 4 is a perspective view of the device after an indicator has been applied, showing the differential manner in which hematin and/or other hemoglobin breakdown products and hemoglobin migrate through the absorbant medium.
FIG. 5 is a perspective view of an alternative embodiment of the invention.

In a preferred embodiment, the fecal occult blood testing device 1 for use in the present invention comprises a base sheet 10 to which is secured a charged, absorbant test medium 20 (FIG. 1). A test sample volume control cover sheet 30 overlies test medium 20 and includes a plurality of openings 31 therein A portion of fecal material wiped onto volume control cover sheet 30 (FIG. 2) passes through openings 31 onto test sheet 20, and the remaining portion of the sample is removed by removing cover sheet 30 (FIG. 3) and disposing of it.

Base sheet 10 is preferably made of a pliable, water-resistant material. By making base sheet 10 pliable, device 1 can be used as a wipe rather than as a receptor upon which a fecal sample is smeared using a small paddle. Of course, in the broader aspects of the invention, the use of a small paddle to smear a sample of fecal material onto device 1 is contemplated. A suitable pliable, water-resistant base sheet is a 3.5 mil (0.0035 inch) thick sheet of vinyl plastic material.

Test medium 20 comprises a sheet of filter paper impregnated with a suspension of charged material such as silica. Since hematin is negatively charged, the silica must be positively charged, which it is at a pH of around 6.4. The key requirement for test medium 20 is that it allow retention of a stool sample, allow the passage of solvent and can be made to carry a charge materially different from either hematin or hemoglobin. Test medium 20 is adhered to base sheet 10 by a suitable adhesive such as an emulsion base acrylic pressure sensitive adhesive.

The specific grade of filter paper is not particularly critical. Medium grade filter paper such as Watman No. 1 is operable.

Numerous silicas are available to those skilled in the chromatography arts, many of which are applicable in the present invention. Aerosil TM 200N is operable. The only requirement for the charged particle material is that it be differentially attractive to hematin and hemoglobin such that separation can be effected. The silica particles are approximately two hundred nanometers in diameter. They comprise a very fine, light powder which is fairly widely used.

Suitable impregnation can be achieved by forming a thin paste of silica in a 70% ethanol and water carrier. This slurry is then pressed into the filter paper with a roller and the paper is allowed to dry.

While impregnating filter paper with silica as described above constitutes the best mode presently contemplated for the invention, it is possible that charged medium can be created by other techniques, as for example treating filter paper with charged organic molecules such as stearates. Another possibility which has not been specifically tested would be to place filter paper in a sulfuric/nitric acid mixture in order to create nitrocellulose paper.

Volume control cover sheet 30 controls the quantity of fecal material which is actually applied to test medium 20. It is a sheet of thin, water-resistant material. A suitable material is a silicone coated tissue paper, at a thickness of about 2 mils. The holes or openings 31 are approximately 0.05 to 0.10 inch in diameter and eight to sixteen such openings are arranged in a pattern in one-half of cover sheet 30. Cover sheet 30 is preferably releasably adhered to test medium 20 along end edge 32 so that it can readily be lifted at end edge 33 and peeled away from test sheet 20 and deposited in the toilet.

Openings 31 are preferably arranged in a circle. The solvent used to facilitate migration can be placed in the approximate center of the circle defined by openings 31 and will tend to flow radially outwardly. The migration of hematin and hemoglobin will thus be in a consistent, radial pattern with respect to the circle of apertures 31.

The solvent 50 must be one which will dissolve hematin and hemoglobin in order the cause them to migrate through the test medium 20. In the preferred embodiment, solvent 50 must also dissolve a buffering agent which helps to ensure an appropriate pH for optimum interaction between the test medium and the hematin. The pH is preferably from about six to about seven, most preferably about 6.4. Sodium acetate is a suitable buffer for this purpose.

Water is a good solvent for hematin and hemoglobin, as well as for the buffer. On the other hand, the solvent preferably includes ethanol, which facilitates the characteristic color change reaction of indicators such as guaiac. The solvent preferably includes between about 60 and about 80% by volume ethanol to facilitate the guaiac or other oxygen colored dye color indication reaction while leaving enough water in the solvent mixture to dissolve the acetate buffer and to facilitate the migration of hematin and hemoglobin. The acetate buffer included in the solution is at a level of about 0.05 Normal.

The means for indicating the presence of hematin and hemoglobin comprise an oxygen colored dye and a peroxide developer which releases oxygen upon exposure to hematin and hemoglobin. The oxygen colored indicator dye reagent can be gum guaiac, orthodianisidine, tetramethylbenzidine, or the like, with guaiac being preferred. The concentration of oxygen colored dye, most preferably guaiac, is from about 5 to about 25 mg./ml., most preferably about 7 mg./ml. The guaiac should not be so concentrated that it either makes the test too sensitive or obscure the peroxidase reaction. If the test is too sensitive, it will detect the minor amounts of blood normally found in the stool. The preferred solvent used is ethanol.

The peroxide solution is preferably about a 1% peroxide solution. The peroxide developer and the indicator dye can be combined in a single solution provided a peroxide stabilizer such as EDTA (ethylene diamine tetraacetic acid) is also included in the solution.

In use, device 1 is preferably used as a wipe in such a way that fecal material is wiped onto volume control cover sheet 30. A portion of the fecal material engages test sheet 20 through volume control openings 31. Cover sheet 30 is lifted from end 33, peeled off at end 32 and disposed of.

Solvent is then applied by dropper 51 approximately, to the center of the circle defined by dots of fecal material 40 on test sheet 20 (FIG. 3). Four drops or about 0.2 ml. of solvent is normally sufficient. As the solvent migrates outwardly through the test medium, it causes hematin 41 and hemoglobin 42 to migrate differently, due to the attractive charges between hematin and the charged test medium 20. About 30 seconds to one minute are allowed for solvent migration. After the solvent has radiated outwardly approximately the distance indicated in FIG. 4, the indicator reagent containing hydrogen peroxide and guaiac or other color indicator is applied to test medium 20. The guaiac colors do indicate the location of hematin 41 and hemoglobin 42 in the manner indicated.

Stool samples which contain only blood from the upper gastrointestinal tract will show color only in close proximity to the test sample dots 40. Thus, in the lower portion of FIG. 4, a showing for hematin 41 only is indicated in close proximity to the adjacent dot of fecal material 40a.

On the other hand, stool samples containing blood only from the lower gastrointestinal tract will tend to form an area 42 extending away from dot 40b of fecal material as indicated in the center of FIG. 4. If the fecal sample contains blood originating in both the upper and the lower gastrointestinal tracts, a mixed pattern will be seen as indicated with the hematin ring 41 and hemoglobin patch 42 radiating away from fecal dot 40c.

The alternative embodiment device 100 (FIG. 5) makes it possible to incorporate a hydrogen peroxide "developer" directly into the solvent system. Alternative embodiment 100 includes a base sheet 110 which is just like base sheet 10. However, sheet 120 differs from test medium sheet 20 in that sheet 120 is a piece of plain, absorbant filter paper. It is not treated with charged particles such as the silica discussed above. It is, however, impregnated with guaiac or other indicator dye.

Figure 6:
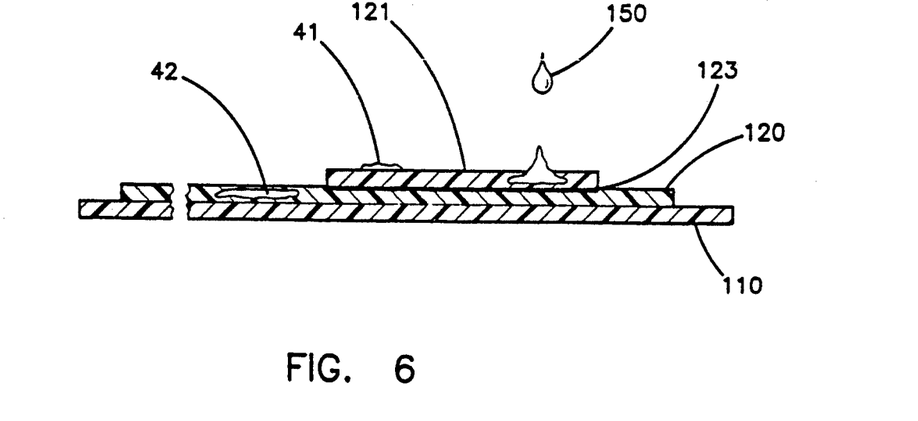
FIG. 6 is a cross-sectional view taken along plane VI—VI of FIG. 5.

A large test dot 121 which is also made of filter paper is impregnated with a suspension of silica in the manner described above. It is adhered to sheet 120 by means of a solvent impermeable adhesive layer 123 (FIG. 6). A fecal sample is applied to test dot 121 through the use of a volume control sheet 130 having openings 131 identical to openings 31, which fall within the circumference of test dot 121 (FIG. 5).

The solvent 150 used in connection with alternative embodiment device 100 contains not only acetate buffer as discussed above, but also 1% hydrogen peroxide. The solvent solution is thus a solvent/developer, whereas in the first embodiment, the migration solvent 50 contains a buffer, but no peroxide.

Figure 7:
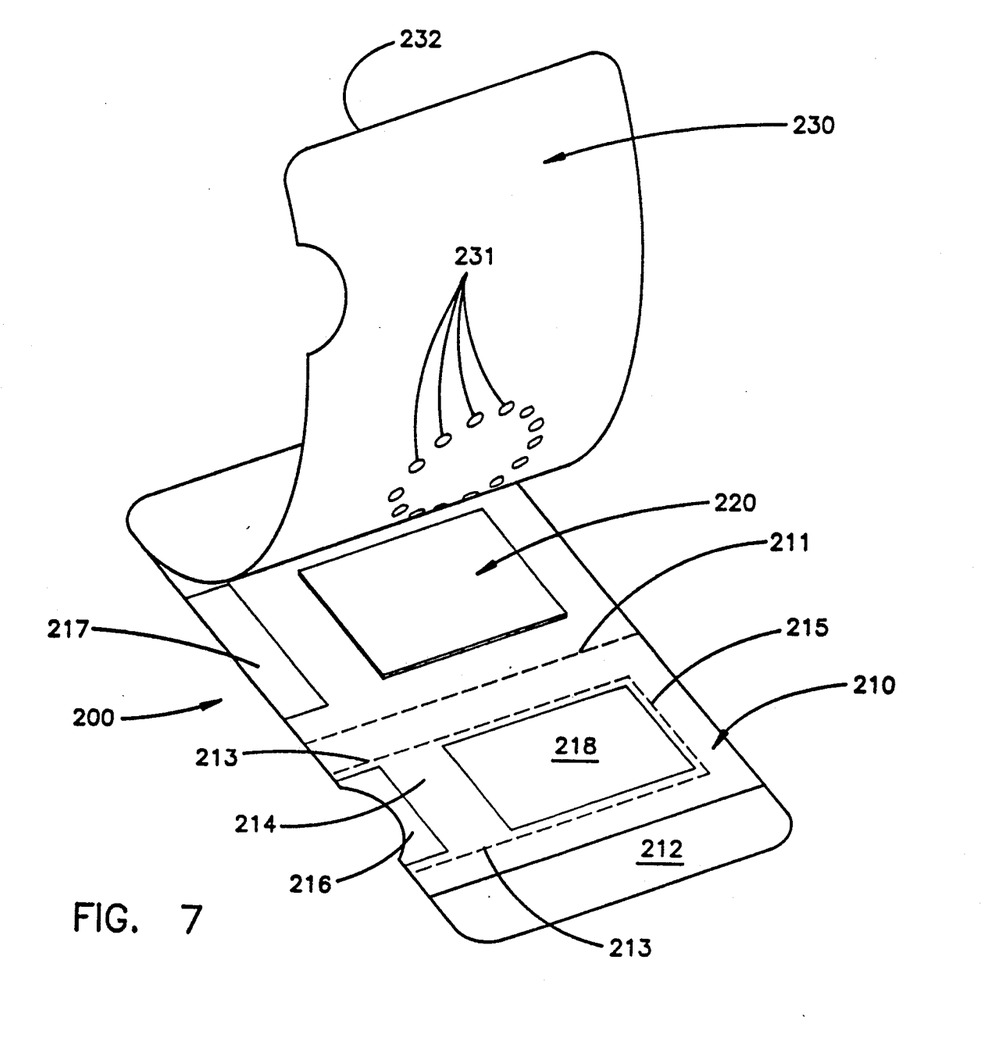
FIG. 7 is a perspective view of another alternative embodiment of the invention.

FIG. 7 discloses yet another alternative embodiment device 200 which comprises a base sheet 210, an absorbant test medium pad 220 and a volume control cover sheet 230 (FIG. 7). Alternative embodiment 200 is designed so that a patient can use the device at home to collect a feces specimen, seal device 200 and bring it or mail it to the doctor or laboratory.

To accomplish the foregoing, pliant base sheet 210 is coated with a pressure sensitive acrylic adhesive as described above, over its entire surface. A fold line 211 is provided laterally across base sheet 210, approximately in the center thereof, by scoring base sheet 210 along fold line 211. A strip of silicone coated release paper 212 is adhered along one end edge of base sheet 210 so that a user can readily grasp the cover sheet 230 along its leading edge 232 when one wants to peel cover sheet 230 off of base sheet 210.

Test medium pad 220 is adhered to the surface of base sheet 210 via the pressure sensitive adhesive. Test pad 220 is located on that half of base sheet 210 which is opposite the end where release liner tab 212 is located.

On that half of base sheet 210 located toward release liner tab 212, base sheet 210 is cut at spaced intervals along parallel lines 213 to define a test door 214. Test door 214 includes a fold line 215 scored in base sheet 210 at the base of door 214. A tab of silicone release paper 216 is placed along the end of door 214 opposite fold line 215 and a matching strip of silicone release paper 217 is located along the same edge of base sheet 210, adjacent test pad 220. In that manner, when base sheet 210 is folded shut along fold line 211, silicone release liner tabs 216 and 217 will line up and will make it possible to slip one's finger or thumb under the end of test door 214 and peel it back away from base sheet 210. Another sheet of silicone release liner 218 is placed on the surface of test door 214 which lines up with test medium pad 220 so that the adhesive on the surface of test door 214 does not peel any portion of test pad 220 away when door 214 is opened.

Test pad 220 can be made exactly like test pad 20 or exactly like test pad 120. In the former case, test pad 220 would be impregnated with silica so as to comprise a charged medium over its entire surface area. In the latter case, test pad 220 would be uncharged, but would include a test dot such as dot 121 in alternative embodiment 100 which would be charged and which would be in alignment with the volume control openings 231 in volume control cover sheet 230.

In use, volume control cover sheet 230 would initially be flat against base sheet 210, covering test door 214 and test pad 220. The patient would wipe with device 200 so that fecal material would pass through volume control openings 231 onto test pad 220. Cover sheet 230 would then be peeled away from base sheet 210 and disposed of. The user would then fold base sheet 210 in half along fold line 211, pressing the two halves against one another so that the pressure sensitive adhesive on the surface of base sheet 210 would seal base sheet 210 closed around the perimeter of test pad 220 containing the dots of fecal material.

The test pad so sealed can then be mailed in an envelope to a laboratory or doctor. The test for fecal occult blood would be conducted in either of the manners described above, depending on whether one used a charged test pad such as test pad 20, or an uncharged test pad with a charged dot such as test pad 120 and dot 121.

The material of base sheet 210 and volume control cover sheet 230 are the same as described above.

Figure 8:
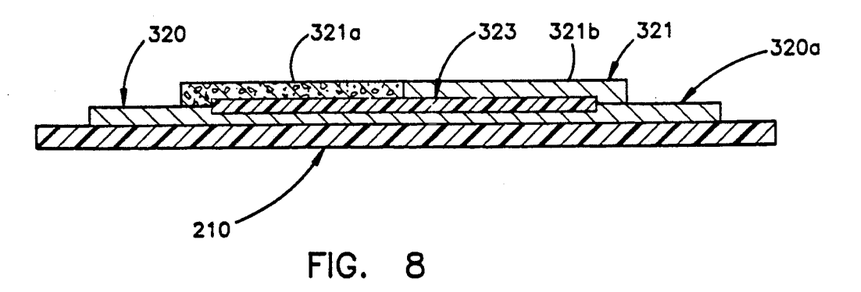
FIG. 8 is a cross-sectional view of another alternative embodiment with the base sheet being partially broken away.
Figure 9:
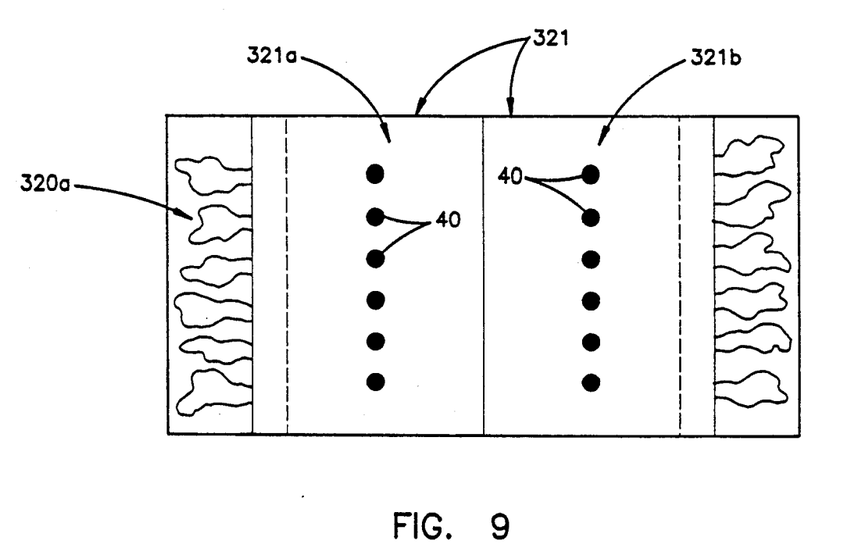
FIG. 9 is a top plan view of the test medium portion of the alternative embodiment as it will look when tested positive for fecal occult blood originating in the lower intestine.
Figure 11:
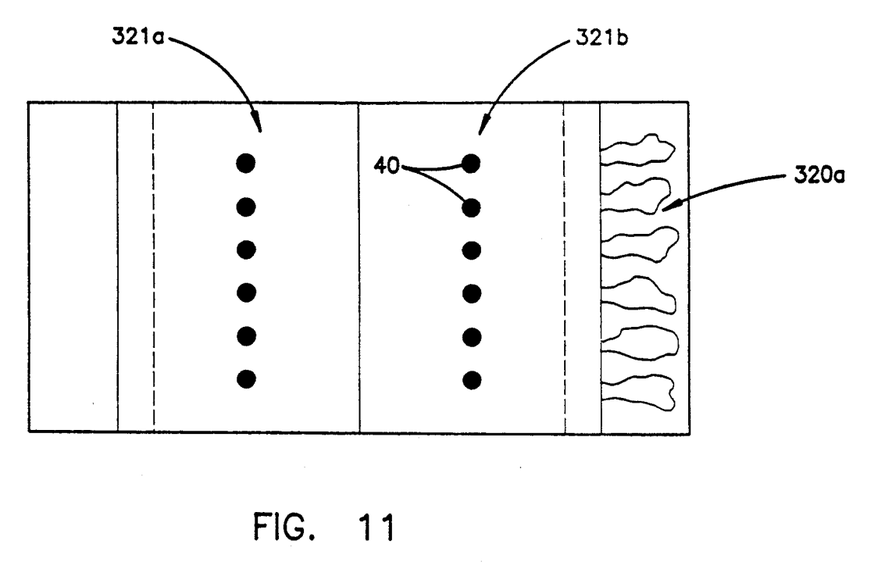
FIG. 11 is a top plan view of the test pad portion of the alternative embodiment device as it appears when tested positive for fecal occult blood originating in the upper intestine only.

FIG. 8 shows an alternative embodiment test pad 320 mounted on base sheet 210 of the alternative embodiment device 200 shown in FIG. 7. It is contemplated that this combination will be the best mode for practicing the invention. Test pad 320 comprises an absorbant sheet of paper 320a which is generally rectangular in configuration (FIGS. 9 and 11). Sheet 320a is impregnated with guaiac indicator dye, also described above. Superimposed over absorbant filter paper 320a is a second rectangular sheet of filter paper 321 which is the same width as sheet 320a, but which is slightly shorter in length such that sheet 320a has an exposed upper surface at each end of sheet 321. Sheet 321 is separated from sheet 320a by a solvent impermeable barrier layer 323 which, like sheets 320a and 321 is generally rectangular in configuration, and is of the same width as sheets 320a and 321. However, solvent impermeable barrier layer 323 is slightly shorter than sheet 321 such that a portion of sheet 321 makes direct contact with sheet 320a at each of the opposed ends of sheet 321.

Sheet 321 is itself divided into two halves, half 321a which is impregnated with a suspension of charged material such as silica, as described above. Silica impregnation in half 321a is illustrated in cross section by small circles in half 321a (compare cross sections of 321a to 321b in FIGS. 8, 10 and 12). The other half 321b is not impregnated with a charged material.

When alternative test pad 320 is used in alternative embodiment device 200, the pattern of holes 231 in volume control cover sheet 230 has to be changed from a circular pattern to two parallel lines of holes. The lines of holes are spaced such that from six to ten openings will overlie each half 321a and 321b of sheet 321. Thus when a user wipes with device 200, six to ten dots of fecal material 40 will be deposited on each half 321a and 321b of sheet 321 (FIG. 9).

Figure 10:
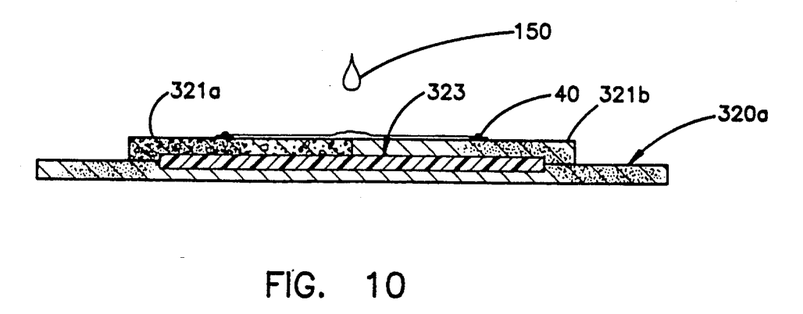
FIG. 10 is a cross-sectional view of the test pad portion of the alternative embodiment as it will appear when tested positive for fecal occult blood originating in the lower intestine.
Figure 12:
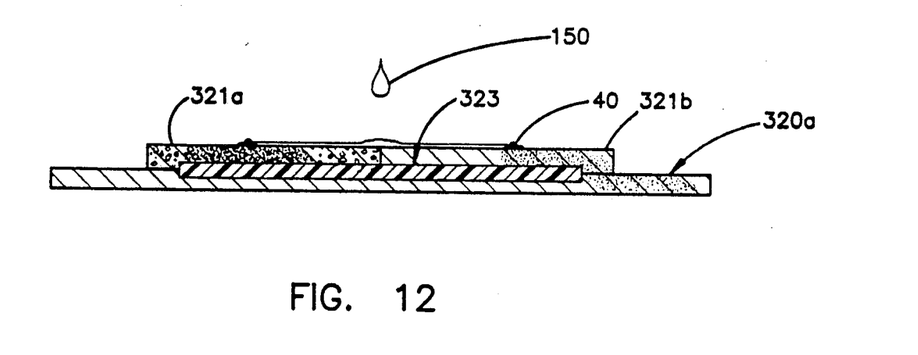
FIG. 12 ia a cross-sectional view thereof.

To determine the fecal occult blood content of the dots of fecal material 40 as applied to test pad 320, several drops of solvent/developer solution 150 are deposited generally along the centerline which divides top sheet 321 into halves 321a and 321b (FIGS. 9 and 10). As discussed above, solvent/developer 150 comprises 0.05 normal acetate buffer and 1% hydrogen peroxide in an ethanol water mixture, wherein ethanol comprises 60 to 80% of volume of the solution (FIGS. 10 and 12). As the solvent developer spreads away from the center of sheet 321, it will carry any hemoglobin present from the lower intestine towards the ends of sheet 321 and past the ends of solvent impermeable barrier 323. The hemoglobin is indicated by shading on FIG. 10. The hemoglobin will thus continue to migrate down into the guaiac impregnated lower sheet 320a where oxygen released by the hemoglobin-peroxide peroxidase reaction will immediately cause the guaiac dye to color blue. Thus blue colored patches will appear at each end of sheet 321, on the exposed ends of sheet 320a (FIG. 9).

In contrast, if the only fecal occult blood in fecal material 40 comes from the upper intestine, it will comprise hematin and other hemoglobin breakdown products which are charged. Alternatively, if only dietary blood or other dietary peroxidase is present, it will also be charged. These charged blood particles will "stick" to the silica impregnated half 321a of sheet 321. Thus, the hematin and hemoglobin breakdown products and other dietary false-positives will not migrate as the solvent/developer 150 passes through them. These materials (indicated by shading in FIG. 12) will not migrate to the left end (as viewed in FIG. 11) of sheet 321. On the other hand, both hematin and hemoglobin breakdown products will migrate through the right half 321b of sheet 321, past the end of barrier 323 and downwardly into the lower guaiac impregnated sheet 320a. Thus where blood in fecal material 40 has originated in the upper intestine, or comprises a dietary false-positive, it will create colored patches only at the right end of guaiac impregnated sheet 320a (FIGS. 11 and 12).

Of course, it is understood that the foregoing is a preferred embodiment of the invention and that various changes and alterations can be made without departing from the spirit and broader aspects thereof.

The embodiments of the invention in which an exclusive property or privilege is claimed are defined as follows.

1. A device for detecting the presence and source of fecal occult blood comprising:
   an impermeable base sheet;
   an absorbent test medium located on said base sheet which will absorb hematin and/or other hemoglobin breakdown products and hemoglobin and which will allow a solution thereof to migrate through said absorbent test medium;
   at least a portion of said absorbent test medium being charged to form a charged medium portion and an uncharged medium portion such that said charged medium portion will differentially attract hematin and/or other hemoglobin breakdown products on the one hand and hemoglobin on the other hand and cause them to migrate differentially through said absorbant test medium when a solvent is applied to said absorbant test medium.

2. The device of claim 1 in which a volume control cover sheet is removably secured to said base sheet over said absorbant test medium; said volume control cover sheet including volume control openings therein located over said charged medium portion.

3. The device of claim 2 in which said absorbant test medium comprises filter paper and said charged medium portion comprises filter paper impregnated with silica.

4. The device of claim 1 in which said absorbant test medium is charged over a large enough area that neither hematin and/or other hemoglobin breakdown products nor hemoglobin will migrate outside of the charged medium portion within a reasonable test time period and using a reasonable quantity of solvent.

5. The device of claim 4 in which said absorbant test medium comprises filter paper and said charged medium portion comprises filter paper impregnated with silica.

6. The device of claim 1 in which said absorbant test medium comprises filter paper and said charged medium portion comprises filter paper impregnated with silica.

7. A device for detecting the presence and source of fecal occult blood comprising:
an impermeable base sheet;
an absorbant test medium located on said base sheet which will absorb hematin and/or other hemoglobin breakdown products and hemoglobin and which will allow a solution thereof to migrate through said absorbant test medium;
at least a portion of said absorbant test medium being charged to form a charged medium portion and an uncharged medium portion such that said charged medium portion will differentially attract hematin and/or other hemoglobin breakdown products on the one hand and hemoglobin on the other hand and cause them to migrate differentially through said absorbant test medium when a solvent is applied to said absorbant test medium; and
a volume control cover sheet removably secured to said base sheet over said absorbant test medium; said volume control cover sheet including volume control openings arranged in a generally circular pattern over said charged portion of said absorbant medium.

8. The device of claim 7 in which said absorbant test medium comprises filter paper and said charged medium portion comprises filter paper impregnated with silica.

9. A device for detecting the presence and source of fecal occult blood comprising:
an impermeable base sheet;
an absorbant test medium located on said base sheet which will absorb hematin and/or other hemoglobin breakdown products and hemoglobin and which will allow a solution thereof to migrate through said absorbant test medium;
at least a portion of said absorbant test medium being charged to form a charged medium portion and an uncharged medium portion such that said charged medium portion will differentially attract hematin and/or other hemoglobin breakdown products on the one hand and hemoglobin on the other hand and cause them to migrate differentially through said absorbant test medium when a solvent is applied to said absorbant test medium; said charged medium portion being a relatively small area such that hematin and/or other hemoglobin breakdown products will not migrate out of said area in a reasonable test period time using a reasonable quantity of solvent, but such that hemoglobin will migrate beyond said charged medium portion; said uncharged medium portion being impregnated with an oxygen colored dye such that after one has caused hemoglobin to migrate into said dye impregnated, uncharged medium portion, a peroxide developer can be applied to said uncharged medium portion to indicate any hemoglobin which has migrated into said uncharged medium portion.

10. The device of claim 9 in which said charged medium portion comprises a first layer of charged medium and said uncharged medium portion comprises a second layer upon which said first layer is adhered with a solvent impermeable layer.

11. The device of claim 10 in which said absorbant test medium comprises filter paper and said charged medium portion comprises filter paper impregnated with silica.

12. The device of claim 9 in which said absorbant test medium comprises filter paper and said charged medium portion comprises filter paper impregnated with silica.

13. A device for use in detecting the presence and source of fecal occult blood comprising:
a pliant, impermeable base sheet which can be folded upon itself approximately across the lateral center thereof so as to define two separate halves which fold over against one another;
an absorbant test medium located on one of said halves of said pliant, impermeable base sheet, at least a portion of said medium being charged to form a charged medium portion and an uncharged medium portion such that said charged medium portion will differentially attract hematin and/or other hemoglobin breakdown products on the one hand and hemoglobin on the other;
an openable test door being located in the other half of said pliant, impermeable base sheet;
sealing means located at least around said absorbant test medium such that when said impermeable base sheet is folded over on itself, it will be sealed closed around said absorbant test medium;
whereby one can test for the presence of hematin and/or other hemoglobin breakdown products and hemoglobin in said absorbant test medium by opening said openable door, placing a solvent on said charged medium portion in the vicinity of a fecal sample collected thereon to cause said solvent to migrate through said absorbant test medium and through any material absorbed from said fecal sample thereby allowing dissolved hematin and/or other hemoglobin breakdown products on the one hand and hemoglobin on the other to migrate differentially through said absorbant test medium, and applying indicating means to cause the visual indication of either hematin and/or other hemoglobin breakdown products on the one hand, hemoglobin on the other, or both in said absorbant medium.

14. The device of claim 13 in which said base sheet is covered generally over its entire surface with a pressure sensitive adhesive, said absorbant test medium being adhered to said base sheet via said pressure sensitive adhesive; at least a portion of the surface area of said test door being covered with a release liner such that when said base sheet is folded over upon itself, pressure sensitive adhesive on said test door will not cause removal of a portion of said absorbant test medium when said door is opened.

15. The device of claim 14 in which a volume control cover sheet is removably secured to said base sheet over said absorbant test medium; said volume control cover sheet including volume control openings therein located over said charged medium portion.

16. The device of claim 15 in which said volume control openings are arranged in a generally circular pattern over said charged portion of absorbant test medium.

17. The device of claim 16 in which said absorbant test medium is charged over a large enough area that neither hematin and/or other hemoglobin breakdown products no hemoglobin will migrate outside of the charged medium portion within a reasonable test time period and using a reasonable quantity of solvent.

18. The device of claim 16 in which said charge medium portion is a relatively small area such that hematin and/or other hemoglobin breakdown products will not migrate out of said area in a reasonable test period time using a reasonable quantity of solvent, but such that hemoglobin will migrate beyond said charged medium portion; said uncharged medium portion being impregnated with an oxygen colored dye such that after one has caused hemoglobin to migrate into said dye impregnated, uncharged medium portion, a peroxide developer can be applied to said uncharged medium portion to indicate any hemoglobin which has migrated into said uncharged medium portion.

19. The device of claim 13 in which said absorbant test medium is charged over a large enough area that neither hematin nor hemoglobin breakdown products nor hemoglobin will migrate outside of the charged medium portion within a reasonable test time period and using a reasonable quantity of solvent.

20. The device of claim 13 in which said charged medium portion is a relatively small area such that hematin and/or other hemoglobin breakdown products will not migrate out of said area in a reasonable test period time using a reasonable quantity of solvent, but such that hemoglobin will migrate beyond said charged medium portion; said uncharged medium portion being impregnated with an oxygen colored dye such that after one has caused hemoglobin to migrate into said dye impregnated, uncharged medium portion, a peroxide developer can be applied to said uncharged medium portion to indicate any hemoglobin which has migrated into said uncharged medium portion 21. A device for detecting the presence and source of fecal occult blood comprising:
a first layer of absorbant medium which will absorb hemoglobin, hematin and/or other hemoglobin breakdown products, said first layer having a length dimension extending between opposed end edges of said first layer;
a fecal occult blood indicator means impregnating said first layer;
a second layer of an absorbant medium which will absorb hemoglobin, hematin and/or other hemoglobin breakdown products, said second layer having opposed ends separated by a length dimension, said length dimension of said second layer being shorter than said length dimension of said first layer;
said second layer being superimposed over said first layer such that the opposed ends of said first layer are spaced outwardly from the opposed ends of said second layer, thereby leaving a portion of said first layer exposed beyond each of said opposed ends of said second layer;
a solvent impermeable layer being interposed between said first and second absorbant layers, said solvent impermeable layer being coextensive with said second absorbant layer, except that said solvent impermeable layer has opposed ends separated by a length dimension which is shorter than said length dimension of said second layer;
said solvent impermeable layer being positioned relative to said second absorbant layer such that each end of said solvent impermeable layer is spaced inwardly from its adjacent end of said second absorbant layer, whereby an end portion of said second absorbant layer beyond each of said ends of said solvent impermeable layer makes direct contact with said first absorbant layer;
a first portion of said second absorbant layer being charged from one of its ends back towards approximately the center of said second absorbant layer to form a charged portion of said second absorbant layer and an uncharged portion of said second absorbant layer such that said charged portion will differentially attract hematin and/or other hemoglobin breakdown products on the one hand, and hemoglobin on the other hand;
whereby when one places a fecal sample on said charged portion of said second absorbant layer and on said uncharged portion of said second absorbant layer and places a solvent for hematin and/or other hemoglobin breakdown products and hemoglobin on said second absorbant layer between said fecal samples in sufficient volume to cause said solvent to migrate through said second absorbant layer and through any material absorbed from said fecal samples, allowing hematin and/or other hemoglobin breakdown products and hemoglobin to migrate from said uncharged portion of said second absorbant layer past the end of said impermeable layer and into said first absorbant layer, said hematin and/or other hemoglobin breakdown products and hemoglobin can be detected through interaction with said indicator means in said first absorbant layer, and whereby said solvent will migrate through said charged portion of said second layer and cause only hemoglobin to migrate through said second absorbant layer, past said end of said solvent impermeable layer and into said first absorbant layer such that its presence can be indicated through interaction with said indicator means in said first absorbant layer.

22. The device of claim 21 in which said indicator means with which said first absorbant layer is impregnated must be activated in order to give a visible indication of the presence of hemoglobin, hemoglobin breakdown product or hematin.

23. The device of claim 22 in which said indicator means comprises an oxygen colored dye.

24. The device of claim 23 in which said oxygen colored dye comprises guaiac.

25. The device of claim 21 which comprises: a pliant impermeable base sheet which can be folded approximately in the middle to define two opposite halves on either side of said fold; said first and second absorbant layers and said solvent impermeable layer being located on one-half of said pliant base sheet; an openable door being located in the other half of said pliant base sheet; sealing means extending at least around the perimeter of said first and second absorbant layers and said impermeable layer such that when said pliant base sheet is folded over on itself, it will seal said first and second absorbant layers and said impermeable layer within said folded over pliant base sheet.

26. The device of claim 25 which includes a removable cover sheet located over said pliant base sheet and said second absorbant layer; volume control openings in said cover sheet, some aligned with said charged portion of said second layer and some aligned with said uncharged portion of said second layer; such that when used with a wiping motion, fecal material passes through said volume control openings in said cover sheet onto said second absorbant layer and said cover sheet can thereafter be removed to allow folding and sealing of said base sheet.

27. The device of claim 21 in which said first and second absorbant layers comprise filter paper and in which said charged portion of said second absorbant layer is charged by being impregnated with silica.

* * * * *

UNITED STATES PATENT AND TRADEMARK OFFICE
CERTIFICATE OF CORRECTION

PATENT NO. : 5,171,528

DATED : December 15, 1992

INVENTOR(S) : Stephen C. Wardlaw et al.

It is certified that error appears in the above-identified patent and that said Letters Patent is hereby corrected as shown below:

Column 2, line 30:
   "a object" should be --an object--.

Column 2, line 47:
   After "hemoglobin" insert --,--.

Column 4, line 9:
   After "therein" insert --,--.

Column 6, line 10:
   "gastrcintestinal" should be --gastrointestinal--.

Column 11, line 21, claim 17:
   "products no" should be --products nor--.

Signed and Sealed this

Tenth Day of May, 1994

*Attest:*

BRUCE LEHMAN

*Attesting Officer*  *Commissioner of Patents and Trademarks*